(12) United States Patent
Lamb

(10) Patent No.: US 7,815,593 B2
(45) Date of Patent: *Oct. 19, 2010

(54) DEVICE FOR INTRODUCING AN OBJECT INTO A VAGINA WITH SANITARY FINGER MOUNTING MEANS

(76) Inventor: Peter James Brian Lamb, 12 Clifford Avenue, Irene (ZA) 1675

( * ) Notice: Subject to any disclaimer, the term of this patent is extended or adjusted under 35 U.S.C. 154(b) by 0 days.

This patent is subject to a terminal disclaimer.

(21) Appl. No.: 11/622,672

(22) Filed: Jan. 12, 2007

(65) Prior Publication Data

US 2007/0118067 A1 May 24, 2007

Related U.S. Application Data

(63) Continuation of application No. 10/486,841, filed as application No. PCT/IB02/03287 on Aug. 16, 2002, now Pat. No. 7,186,248.

(30) Foreign Application Priority Data

Aug. 16, 2001 (ZA) .................................. 2001/6784

(51) Int. Cl.
*A61F 13/26* (2006.01)
(52) U.S. Cl. ...................... 604/13; 604/385.17; 604/904
(58) Field of Classification Search ............. 604/11–13, 604/15, 17, 385.17, 904; 206/529, 531, 571
See application file for complete search history.

(56) References Cited

U.S. PATENT DOCUMENTS

| 1,224,735 | A | * | 5/1917 | Gamache | 604/15 |
|---|---|---|---|---|---|
| 1,537,257 | A | * | 5/1925 | Mizner | 604/15 |
| 1,969,671 | A | * | 8/1934 | Archer | 604/14 |
| 2,351,836 | A | | 6/1944 | Popper | 604/16 |
| 2,355,917 | A | * | 8/1944 | Knight | 604/11 |
| 2,450,138 | A | * | 9/1948 | Harwood | 604/15 |
| 2,856,928 | A | * | 10/1958 | Zener | 604/59 |
| 2,884,925 | A | * | 5/1959 | Meynier, Jr | 604/14 |
| 3,058,469 | A | * | 10/1962 | Crockford | 604/363 |
| 3,059,642 | A | | 10/1962 | Gershen | 604/17 |
| 3,196,873 | A | * | 7/1965 | Bletzinger et al. | 604/15 |
| 3,358,686 | A | * | 12/1967 | Kunitami | 604/14 |
| 3,409,011 | A | * | 11/1968 | Heinz | 604/15 |
| 3,643,661 | A | * | 2/1972 | Crockford | 604/15 |
| 3,674,029 | A | * | 7/1972 | Bates et al. | 604/366 |
| 3,765,417 | A | * | 10/1973 | Crockford | 604/15 |
| 3,835,856 | A | * | 9/1974 | Warncke | 604/15 |
| 3,885,563 | A | * | 5/1975 | Johnson et al. | 604/14 |
| 3,918,452 | A | | 11/1975 | Cornfeld | 604/515 |

(Continued)

FOREIGN PATENT DOCUMENTS

DE           436588 C        11/1926

(Continued)

*Primary Examiner*—Tatyana Zalukaeva
*Assistant Examiner*—Paula L Craig
(74) *Attorney, Agent, or Firm*—Woodcock Washburn LLP

(57) ABSTRACT

A device for introducing an object into a vagina includes finger mounting means whereby the device is mountable on a user's finger, and a holder which protrudes from the finger mounting means and which is insertable into a user's vagina, the holder being configured to hold an object whilst being inserted into the user's vagina and then release the object once positioned inside the vagina.

12 Claims, 2 Drawing Sheets

U.S. PATENT DOCUMENTS

| | | | | |
|---|---|---|---|---|
| 3,946,737 A * | 3/1976 | Kobler | | 604/385.18 |
| 3,998,225 A * | 12/1976 | Hytonen | | 604/11 |
| 4,212,301 A * | 7/1980 | Johnson | | 604/385.18 |
| 4,269,187 A | 5/1981 | Sakurai et al. | | 604/14 |
| 4,286,594 A * | 9/1981 | Cunningham | | 604/15 |
| 4,361,150 A * | 11/1982 | Voss | | 604/15 |
| 4,498,899 A * | 2/1985 | Gross | | 604/16 |
| 4,536,178 A * | 8/1985 | Lichstein et al. | | 604/15 |
| 4,543,086 A * | 9/1985 | Johnson | | 604/11 |
| 4,592,740 A * | 6/1986 | Mahruki | | 604/15 |
| 4,726,805 A * | 2/1988 | Sanders, III | | 604/15 |
| 4,755,166 A * | 7/1988 | Olmstead | | 604/11 |
| 4,891,042 A | 1/1990 | Melvin et al. | | 604/18 |
| 5,105,827 A * | 4/1992 | Augros | | 128/832 |
| 5,153,971 A * | 10/1992 | Van Iten | | 28/1.18 |
| 5,158,535 A * | 10/1992 | Paul et al. | | 604/15 |
| 5,507,807 A * | 4/1996 | Shippert | | 623/8 |
| 5,788,910 A | 8/1998 | McNelis et al. | | 264/296 |
| 5,891,081 A * | 4/1999 | McNelis et al. | | 604/14 |
| 5,891,123 A * | 4/1999 | Balzar | | 604/385.18 |
| 6,019,743 A * | 2/2000 | Cole et al. | | 604/15 |
| 6,071,259 A * | 6/2000 | Steiger et al. | | 604/11 |
| 6,162,203 A * | 12/2000 | Haaga | | 604/272 |
| 6,186,973 B1 | 2/2001 | Buzot | | 604/14 |
| 6,254,566 B1 * | 7/2001 | Buck et al. | | 604/15 |
| 6,283,952 B1 * | 9/2001 | Child et al. | | 604/540 |
| 6,508,780 B1 * | 1/2003 | Edgett et al. | | 604/15 |
| 6,533,748 B2 * | 3/2003 | Buzot | | 604/15 |
| 6,582,389 B2 * | 6/2003 | Buzot | | 604/15 |
| 6,645,136 B1 * | 11/2003 | Zunker et al. | | 600/29 |
| 6,786,883 B2 * | 9/2004 | Shippert | | 604/15 |
| 6,939,289 B2 * | 9/2005 | Zunker et al. | | 600/29 |
| 7,118,550 B2 * | 10/2006 | Loomis | | 604/60 |
| 7,172,573 B1 * | 2/2007 | Lamb | | 604/59 |
| 7,186,248 B2 * | 3/2007 | Lamb | | 604/11 |

FOREIGN PATENT DOCUMENTS

| | | |
|---|---|---|
| EP | 0 064 747 A2 | 11/1982 |
| FR | 868 718 A | 1/1942 |
| GB | 2 204 495 A | 11/1988 |
| GB | 2 227 666 A | 8/1990 |
| WO | WO 99/52576 A1 | 10/1999 |

* cited by examiner

DEVICE FOR INTRODUCING AN OBJECT INTO A VAGINA WITH SANITARY FINGER MOUNTING MEANS

This is a continuation of application Ser. No. 10/486,841 filed Jun. 22, 2004, which is a U.S. National Phase of PCT/IB02/03287 filed Aug. 16, 2002, which claims priority to South Africa application number 2001/6784 filed Aug. 16, 2001.

BACKGROUND OF THE INVENTION

THIS INVENTION relates to a device for introducing an object into a vagina.

The Inventor is aware of two methods of inserting a tampon into a vagina. In the first method, the user manipulates the tampon by hand and effectively pushes it into her vagina making use of her finger. One disadvantage with this method is that in order to insert the tampon to a sufficient depth, at least a portion of a user's finger must be inserted into the vagina. Naturally, this is unhygienic and undesirable.

The problem is partially overcome by the second method which includes using a paper or plastic applicator comprising an outer tube in which a tampon is mounted and an inner tube which is slidable inside the outer tube and functions as a plunger to displace the tampon from the inner tube once the inner tube has been inserted into the vagina.

However, this method suffers from the disadvantage that the applicator is of a hard and non-pliable material so that there is little or no bend or give during insertion of the device into a vagina. This rigidity makes vaginal insertions more difficult and painful. Often women do not know that the vagina is angled upwards from its opening and that it is not horizontal. After inserting a leading end of the applicator through the vaginal opening in the horizontal direction, the leading end collides with the back wall of the vagina, which is painful and causes the user to think that the applicator has reached the limit of the vagina. The user then deposits the tampon in the vagina at too shallow a depth leading to discomfort.

Further, both methods suffer from the disadvantage that during insertion, a leading end of the tampon is exposed. This results in moisture being absorbed increasing friction between vaginal wall and tampon and so making vaginal insertion more difficult and possibly resulting in malpresentation (incorrect alignment) of the tampon in the vagina. The latter may cause pain or "loss" of the tampon in the vagina.

It is an object of this invention to provide means which the Inventor believes will at least alleviate at least some of these problems.

SUMMARY

According to the invention there is provided a device for introducing an object into a vagina which device includes finger mounting means whereby the device is mountable on a user's finger; and a holder which protrudes from the finger mounting means and which is insertable into a user's vagina, the holder being configured to hold an object whilst being inserted into the user's vagina and then release the object once positioned inside the vagina.

The Inventor believes the device will find application particularly for use in the digital vaginal insertion of tampons. However, the Inventor believes the device will be suitable, with or without modification, for the insertion of other objects such as ovules, suppositories and the like.

The device may include an elongate body, the finger mounting means being in the form of a socket extending longitudinally inwardly from an operatively trailing end of the body within which socket at least an end portion of a user's finger is snugly receivable. A nail receiving recess may lead from the socket. The nail receiving recess serves both to accommodate a user's finger nail and to orientate the device relative to a user's finger.

Naturally, the configuration of the holder will depend on the configuration of the object being inserted.

When the object being inserted is a tampon, the holder may include a cradle within which a tampon is receivable, the cradle being configured such that when a tampon is inserted in the cradle, at least part of the tampon intermediate its ends is exposed.

A leading end of the holder which forms a leading end of the body may be configured to cover a leading end of the tampon. In addition, the leading end of the body may be generally domed to facilitate insertion thereof into a vagina. The leading end of the body may have the general shape or may incorporate at least some of the design features of a glans penis. Thus, the leading end of the body may have a rounded point which flares back like the corona of a glans penis and which in use lifts the opposing vaginal wall when the body is inserted in a vagina by a wedging action.

The leading end of the body may be split and formed of a flexible material to permit the passage of a tampon therethrough when the device is withdrawn from a user's vagina permitting a tampon to remain in position in the vagina.

The holder may define a seat or recess within which a trailing end of a tampon is receivable.

The socket and the holder may be disposed angularly relative to one another. More particularly, a longitudinal axis of the socket and a longitudinal axis of the holder may be arranged at an obtuse angle relative to one another. The obtuse angle may be between 170° and 135°. Preferably, the obtuse angle is between 160° and 140°, and most preferably between 155° and 145°, and is thus selected to compensate for the angle of vaginal inclination.

The device may include a flexible cover protruding from the trailing end of the body to cover the portion of a user's finger not inserted into the socket and the perineum and the area of the vulva which may come into contact with the user's other fingers.

The socket will typically have a depth which is sufficient to accommodate at least an end portion of a user's finger, typically a middle finger, up to the first phalanx. Hence, the socket will typically have a depth of between 1.5 and 2.5 cm, typically 2 cm. Further, the socket will typically have lateral dimensions of about 1.5 cm.

The holder will typically have a length of between 1.5 and 8 cm, typically 5.5 cm.

The body will typically be formed as a moulding of a synthetic plastics material or polymeric material, such as silicone rubber, or thermoplastic material or paper having a suitable hardness. The desired rigidity of the body at various positions may be achieved by varying the thickness of the body.

BRIEF DESCRIPTION OF THE FIGURES

The invention will now be described, by way of example, with reference to the accompanying diagrammatic drawings.

In the drawings.

DETAILED DESCRIPTION OF EMBODIMENTS

Figure 1:
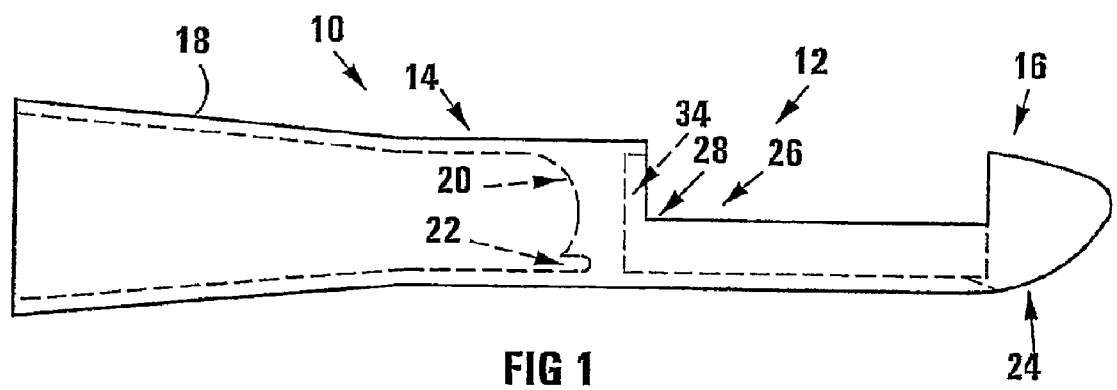
FIG. 1 shows a side view of a device in accordance with the invention.

In FIGS. 1 to 4 of the drawings, reference numeral 10 refers generally to a device for introducing an object into a vagina in accordance with the invention.

The device 10 includes an elongate body 12 having a trailing end 14 and a leading end 16. A flexible cover or skirt 18 protrudes from a trailing end 14 of the body 12.

A socket 20 extends longitudinally inwardly from a trailing end 14 of the body 12. The socket 20 is dimensioned such that an end portion of a user's finger, typically a middle finger, is snugly receivable therein such that the body 12 effectively forms an extension of the user's finger. A nail receiving recess 22 extends from the socket 20 to accommodate a user's finger nail. The nail receiving recess 22 also serves to orientate the body 12 relative to a user's finger as described in more detail herebelow.

A lower part of the body is shaped to be similar to the shape of a lower part of a penis. The leading end 16 of the body 12 generally has the shape of a glans penis. As can best be seen in FIG. 1 of the drawings, a bottom surface 24 of the leading end 16 is curved in side view to inhibit abrasion of the posterior vaginal wall in use. The leading end of the body thus has a rounded point which flares back like the corona of a glans penis which in use lifts and wedges the opposing vaginal walls apart when the body 12 is inserted into a vagina.

The portion of the body 12 extending forwardly from the socket 20 forms a holder in the form of a cradle, generally indicated by reference numeral 26. The cradle 26 defines a circular cylindrical recess 28 within which a tampon 30 is snugly receivable. A longitudinally extending upper portion of the body 12 is open such that a substantial portion of a tampon inserted into the recess 28 is exposed. The cradle 26 defines a seat 34 within which a trailing end portion of the tampon 30 is receivable.

Figure 2:
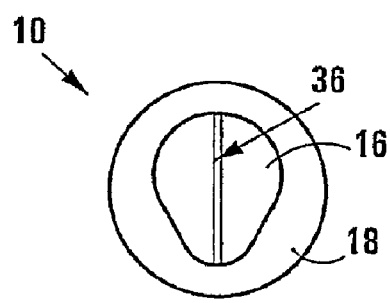
FIG. 2 shows a front view of the device of FIG. 1.

The leading end 16 of the body 12 is provided with a slit 36 (FIG. 2). The slit permits a tampon to be released from the cradle 26 through the leading end of the body 12 as is described in more detail herebelow.

As can clearly be seen in FIG. 1 of the drawings, the nail receiving recess 22 and the recess 28 are disposed on opposite sides of the body 12 such that, in use, the recess 28 is on that side of the finger corresponding to the inner surface of the finger.

Figure 3:
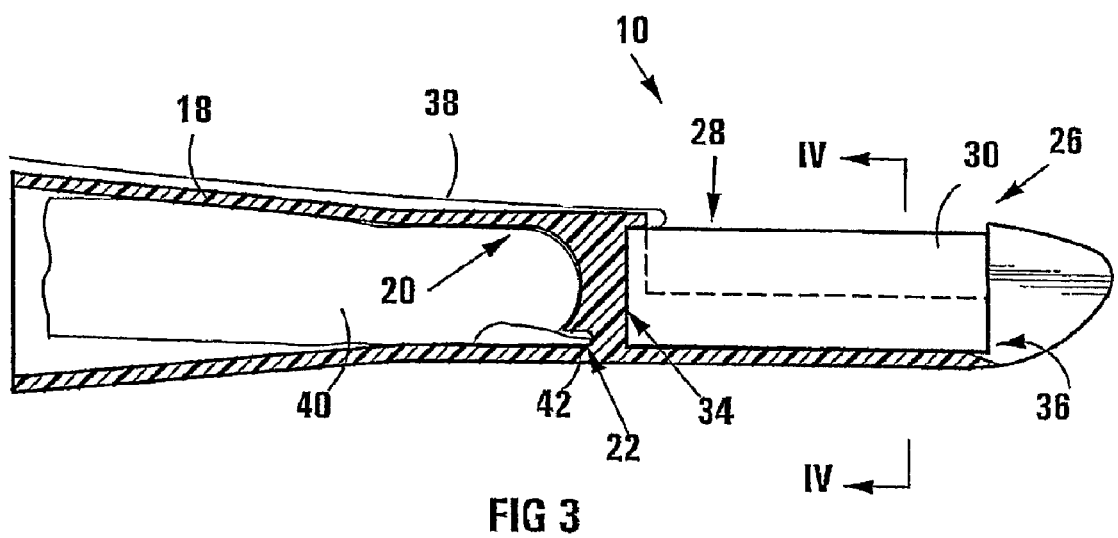
FIG. 3 shows a longitudinal sectional view of the device of FIG. 1.
Figure 4:
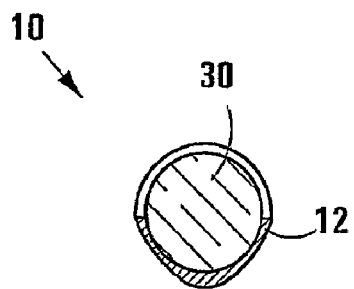
FIG. 4 shows a sectional elevation taken at IV-IV in FIG. 3.

In use, a tampon 30 is positioned in the recess 28 as shown in FIG. 3 of the drawings. A retrieval string 38 attached to a trailing end of the tampon 30 is positioned such that it runs along the outside of the body 12 and cover 18.

A user's finger is inserted into the socket 20 with the finger nail 42 positioned in or in register with the nail receiving recess 22.

Figure 6:
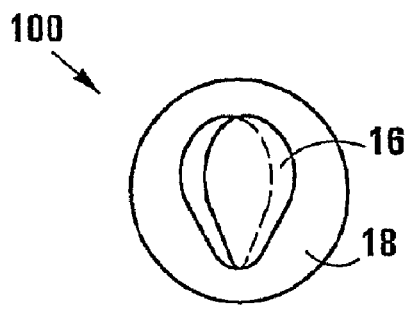
FIG. 6 shows a front view similar to FIG. 2 of another device in accordance with the invention.

The user then inserts the body 12, leading end 16 first, into her vagina. By virtue of the shape of the leading end 16, the two sides of the leading end are urged towards one another as the body 12 is inserted thereby effectively closing the slit 36 and preventing the passage of the tampon 30 therethrough. In another embodiment, shown in FIG. 6, the two sides of a leading end 16 of a device 100 overlap to prevent the passage of a tampon therethrough during insertion of the device 100.

Once the body 12 has been fully inserted, the finger is twisted to dislodge the tampon 28 from the body which is then gently withdrawn from the user's vagina. By virtue of the fact that a substantial portion of the tampon 30 intermediate its ends is exposed, friction between the tampon and the vagina tends to retain the tampon 30 in position. The flexibility of the leading end 16 of the body 12 is selected such that as the body 12 is removed, the two sides of the leading end open up to permit the tampon 30 to pass therethrough and remain in the vagina in the desired position.

The device 10, 100 can then either be washed for re-use or disposed of. In the case of a disposable device 10, 100, it may be pre-packaged with a tampon 30 in position in the recess 28.

Figure 5:
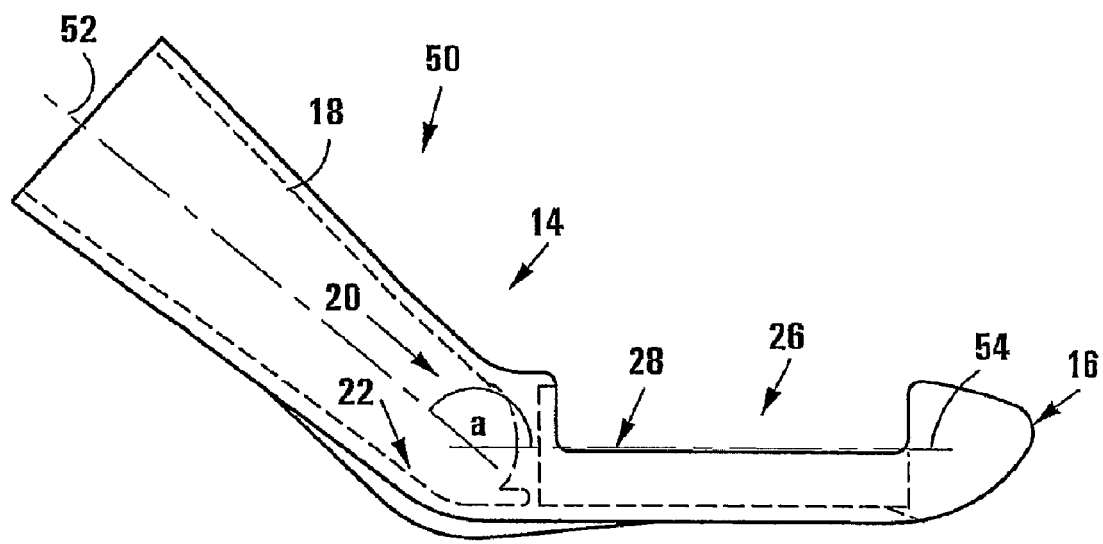
FIG. 5 shows a side view, similar to FIG. 1, of another device in accordance with the invention.

Reference is now made to FIG. 5 of the drawings, in which reference numeral 50 refers generally to another device in accordance with the invention and, unless otherwise indicated, the same reference numerals used above are used to designate similar parts.

The main difference between the device 50 and the device 10 is that, in the case of the device 50, a longitudinal axis 52 of the socket 20 and a longitudinal axis 54 of the cradle 26 are disposed at an angle relative to one another. The angle is typically about 150°. This corresponds to the angle of inclination of the vagina of a standing woman relative to the horizontal and thereby facilitates correct alignment of the tampon for introduction into the vaginal introitus.

The connection between the part of the body 12 in which the socket 20 is provided and the part of the body 12 defining the cradle is sufficiently flexible to permit the portion of the body 12 in which the socket 20 is provided to be displaced angularly so that the axes 52, 54 can be brought more-or-less into line to facilitate full insertion of the body 12.

This arrangement serves to indicate to the user the correct direction in which the body should be introduced through the introitus and the direction in which the straightened body should be displaced along the vaginal cavity.

The Inventor believes that the device 10, 50 includes the following advantages:

The length of the body 12 is not intimidating, but nonetheless provides effective depth of deposition of the tampon or other object into the vagina. The body 12 is of a relatively soft, elastic material which is less difficult and painful to insert than applicators of which the Inventor is aware. Further, the cross-section of the body 12 is easier and more comfortable to insert into a vagina. Friction against the back wall of the vagina is reduced due to the shape of the holder.

Further, the glans penis like leading end 16 of the body 12 is easier and more comfortable to insert than the leading end portions of conventional devices. In addition, the shape of the leading end reduces the risk of micro-trauma on the vaginal wall and hence reduces the risk of infection.

In addition, in the device 50, the angle of the socket 20 relative to the holder 26 promotes easier introduction of the holder through the introitus and indicates the direction for its advancement up the vagina. There is a built-in correction for the directional inclination of the vaginal cavity, which causes less risk of injury and discomfort to the user. The holder can be inserted while the user is sitting or standing and the procedure is therefor much easier and more comfortable to accomplish physically and much less an affront to a female's dignity.

In addition, the provision of the cover 18 avoids the user's hand coming into contact with vaginal discharge thereby improving hygiene and reducing the risk of transmission of diseases such as hepatitis and the like. The procedure is more pleasing aesthetically because it avoids contamination of the user's finger and nail by menstrual fluids or vaginal discharge.

The invention claimed is:

1. A digital tampon insertion device and tampon combination which includes
an elongate socket formation defining a socket within which at least an end portion of a user's finger is securely receivable, the socket formation having an opening at a free end thereof through which a user's finger is inserted in use;
an elongate tampon; and
an elongate tampon holder which extends away from an end of the socket formation remote from said opening of said socket formation,
the tampon holder including a cradle, the cradle having opposing upper longitudinal edges and a longitudinal axis, the cradle defining an elongate recess having a length and a cross-sectional profile transverse to said length, the edges being substantially parallel to the longitudinal axis of the cradle,
the tampon being positioned in the elongate recess defined by the cradle, so that:
(i) a longitudinally extending part cylindrical portion of a surface of the tampon is covered and a longitudinally extending part cylindrical portion of a surface of the tampon is exposed, the part cylindrical surface portions merging with one another in a plane dissecting the tampon longitudinally,
(ii) a line drawn between the opposing upper longitudinal edges of the cradle dissects the cross-sectional profile of the tampon, and
(iii) said exposed surface portion of the tampon during use of the device is in frictional contact with the vagina,
the tampon holder having an open or openable free end remote from the socket formation through which the tampon can pass on withdrawal of the device from a vagina, due to friction between the exposed surface portion of the tampon and the vagina,
and in which the socket formation defines said socket and a further recess which is a nail receiving recess leading from the socket towards the tampon holder, the nail receiving recess having a fixed circumferential location relative to the socket, the nail receiving recess being configured to circumferentially orient the socket relative to a user's finger, the nail receiving recess in use is oriented opposite the exposed surface portion of the tampon and receives a finger nail of a user thereby circumferentially to orientate the device relative to the user's finger to ensure that the exposed surface portion of the tampon is on a side of a user's finger corresponding to the inner surface of the finger.

2. The combination of claim 1, in which a longitudinal axis of the socket formation and a longitudinal axis of the tampon holder are disposed at an obtuse angle relative to one another.

3. The combination of claim 1, in which the socket formation is configured to prevent contact between a user's finger received in the socket and the tampon positioned in the elongate recess defined by the cradle.

4. A digital tampon insertion device which includes
an elongate socket formation defining a socket within which at least an end portion of a user's finger is securely receivable, the socket formation having an opening at a free end thereof through which a user's finger is inserted in use; and
an elongate rigid tampon holder which protrudes forward from the socket formation,
the tampon holder including a cradle having opposing upper longitudinal edges, the cradle defining an elongate recess configured to hold an elongate tampon having a length and a cross-sectional profile transverse to said length,
the tampon holder being configured to cover a longitudinally extending surface portion of the tampon from one end of the tampon to the other end of the tampon, and at the same time to leave exposed a longitudinally extending surface portion of the tampon intermediate the ends of the tampon,
so that a line drawn between the opposing upper longitudinal edges of the cradle dissects the cross-sectional profile of the tampon,
with said exposed surface portion of the tampon during use of the device being in frictional contact with the vagina,
the tampon holder having an open or openable free end remote from the socket formation through which the tampon can pass on withdrawal of the device from a vagina, due to friction between the exposed surface portion of the tampon and the vagina,
and in which the socket formation defines said socket and a further recess which is a nail receiving recess leading from the socket towards the tampon holder, the nail receiving recess having a fixed circumferential location relative to the socket, the nail receiving recess being configured to circumferentially orient the socket relative to a user's finger, the nail receiving recess in use is oriented opposite the exposed surface portion of the tampon and receives a finger nail of a user thereby circumferentially to orientate the device relative to the user's finger to ensure that the exposed surface portion of the tampon is on a side of a user's finger corresponding to the inner surface of the finger.

5. The digital tampon insertion device as claimed in claim 4, in which a longitudinal axis of the socket formation and a longitudinal axis of the tampon holder are disposed at an obtuse angle relative to one another.

6. The digital tampon insertion device as claimed in claim 4, in which the socket formation is configured to prevent contact between a user's finger received in the socket and a tampon received in the tampon holder.

7. A digital tampon insertion device which includes
an elongate socket formation defining a socket within which at least an end portion of a user's finger is securely receivable, the socket formation having an opening at a free end thereof through which a user's finger is inserted in use; and
an elongate tampon holder fast with the socket formation,
the tampon holder including a cradle, the cradle having opposing upper longitudinal edges and a longitudinal axis, the cradle defining a recess configured to hold a tampon having a length and a cross-sectional profile transverse to said length, the edges being substantially parallel to the longitudinal axis of the cradle,
so that a part circumferentially extending first surface portion of the tampon is seated in the recess and a part circumferentially extending second surface portion of the tampon is exposed, the part cylindrical circumferentially extending surface portions merging with one another in a plane dissecting the tampon longitudinally,
so that a line drawn between the opposing upper longitudinal edges of the cradle dissects the cross-sectional profile of the tampon,
with said exposed second surface portion of the tampon during use of the device being in frictional contact with the vagina, the tampon holder having an open or openable free end remote from the socket formation through which the tampon can pass on withdrawal of the device from a vagina, due to friction between the exposed second surface portion of the tampon and the vagina, and in which the socket formation defines said socket and a further recess which is a nail receiving recess leading from the socket towards the tampon holder, the nail receiving recess having a fixed circumferential location relative to the socket, the nail receiving recess being configured to circumferentially orient the socket relative to a user's finger, the nail receiving recess in use is oriented opposite the exposed second surface portion of the tampon and receives a finger nail of a user thereby circumferentially to orientate the device relative to the user's finger to ensure that the exposed second surface portion of the tampon is on a side of a user's finger corresponding to the inner surface of the finger.

8. The digital tampon insertion device as claimed in claim 7, in which a longitudinal axis of the socket formation and a longitudinal axis of the tampon holder are disposed at an obtuse angle relative to one another.

9. The digital tampon insertion device as claimed in claim 7, in which the socket formation is configured to prevent contact between a user's finger received in the socket and a tampon received in the tampon holder.

10. A digital tampon insertion device which includes
an elongate tampon holder defining a recess within which a tampon is receivable so that a part circumferentially extending surface portion of the tampon is seated in the recess and a part circumferentially extending second surface portion of the tampon is exposed; and
an elongated socket formation fast with an end of the tampon holder,
the socket formation defining a first socket which opens with an opening away from the tampon holder within which a portion of a user's finger is securely receivable,
the socket formation having an orientation formation which serves to locate the device on a user's finger and is configured to orientate the tampon holder circumferentially relative to a user's finger,
the orientation formation being a second socket configured to receive a finger nail of said finger of a user received in the first socket, said second socket leading from the first socket towards the tampon holder, said second socket having a fixed circumferential location relative to the first socket, said second socket in use being oriented opposite the exposed second surface portion of the tampon and receiving said finger nail of the user's finger received in the first socket thereby circumferentially to orientate the device relative to the user's finger received in the first socket to ensure that the exposed second surface portion of the tampon is on a side of said finger received in the first socket corresponding to the inner surface of said finger.

11. The digital tampon insertion device as claimed in claim 10, with said exposed second surface portion of the tampon during use of the device being in frictional contact with the vagina.

12. The digital tampon insertion device as claimed in claim 10, in which the first socket formation is configured to prevent contact between a user's finger received in the socket and a tampon received in the tampon holder.

* * * * *

UNITED STATES PATENT AND TRADEMARK OFFICE
CERTIFICATE OF CORRECTION

PATENT NO. : 7,815,593 B2  Page 1 of 1
APPLICATION NO. : 11/622672
DATED : October 19, 2010
INVENTOR(S) : Peter James Brian Lamb It is certified that error appears in the above-identified patent and that said Letters Patent is hereby corrected as shown below:

Column 6,
Line 58, after "the part" delete "cylindrical".

Signed and Sealed this
Twenty-seventh Day of September, 2011

David J. Kappos
*Director of the United States Patent and Trademark Office*